United States Patent [19]

Lindsey

[11] Patent Number: 4,654,466
[45] Date of Patent: Mar. 31, 1987

[54] INBRED CORN LINE
[75] Inventor: Marvin F. Lindsey, Boone, Iowa
[73] Assignee: Dekalb-Pfizer Genetics, Ill.
[21] Appl. No.: 728,534
[22] Filed: Apr. 29, 1985
[51] Int. Cl.$^4$ .............................................. A01H 1/06
[52] U.S. Cl. ........................................ 800/1; 47/58; 47/DIG. 1
[58] Field of Search ................. 47/58, DIG. 1; 800/1
[56] References Cited

U.S. PATENT DOCUMENTS 4,607,453  8/1986  Troyer ................................. 47/58

Primary Examiner—Robert E. Bagwill
Attorney, Agent, or Firm—Charles J. Knuth; Peter C. Richardson; James H. Monroe

[57] ABSTRACT

This invention relates to an inbred line of corn having the designation 78010, seeds produced by plants of the inbred line 78010, cells which upon growth and differentiation produces the inbred line 78010, hybrid corn seed produced by crossing the inbred line 78010 with another corn line and a process for the production of hybrid corn seed using the inbred line 78010.

10 Claims, No Drawings

INBRED CORN LINE

BACKGROUND OF THE INVENTION

*Zea mays* or corn is an agronomically important crop in many countries of the world and is extremely commercially important in the United States. Corn is used for feed, for food and for industrial purposes.

Within the past 60 years, hybrid corn has become commercially dominant. As a result of the hybridization of corn, varieties with markedly improved yields, better stalks, better roots, markedly more uniform characteristics, and improved resistance to insect and disease pests have been developed.

Single cross hybrid corn is produced by using a homozygous inbred line as the parent. Homozygosity in an inbred line is achieved by repeated inbreeding and in general, by the sixth or seventh generation the inbred line is considered genetically pure. Unfortunately, a reduction in performance, yield and other plant characteristics, which are desirable, arises as a result of the inbreeding to achieve essentially genetic identity. As a result, these inbred corn lines are not grown as a commercial crop.

Although inbred lines which have been developed by various breeders in corn research are not grown as a commercial crop, they are extremely important because they are employed to produce first generation ($F_1$) hybrids by the hybridization of, for example, two inbred lines as parents. As a result of the crossing of the two inbred lines, hybrid vigor or heterosis arises and the hybrid plants produced have markedly improved yields, better stalks, better roots, better uniformity and better insect and disease resistance. Further, as a result of self-pollination of $F_1$ hybrid plants or cross-pollination of $F_1$ hybrid plants, a second generation ($F_2$) hybrid occurs. The $F_2$ hybrid plant, and seed produced thereby, has characteristics which are less desirable than those of the $F_1$ hybrid, for example, lower yields, and expression of undesirable genetic traits results. Due to this reduced performance, seed from $F_1$ hybrids which produces less advantageous second generation $F_2$ hybrids is not saved by farmers. Rather, new hybrid seed produced by crossing the originally selected inbred parents to produce the first generation hybrid ($F_1$) seed is purchased from commercial seed companies by farmers each year for their planting.

The selection and production of inbred lines as parents which when crossed provide superior and improved $F_1$ hybrids is a specialized and highly skilled area. Not only must a corn breeder select and develop superior inbred parental lines, but the corn breeder must also be able to produce and select hybrid combinations of these inbred lines which will produce desirable $F_1$ hybrids which will be commercially successful.

As a result of the necessity to utilize inbred parental lines to produce commercially desirable and successful $F_1$ corn hybrids, great emphasis is placed in corn breeding and hybridization on developing the necessary inbred parental lines. As a result, it is essential to select and develop new inbred lines which when used in hybridization will provide improvements in first generation hybrid corn characteristics in terms of increased yield, improved plant stability, improved resistance to disease and other insect pests, uniformity in appearance to thereby permit easy mechanical harvesting and maximization of harvesting efforts with a minimization of labor involved, etc.

As a result, a concerted effort exists in the production of commercially successful first generation corn hybrids to develop the necessary inbred lines as parental stock.

SUMMARY OF THE INVENTION

Accordingly, an object of this invention is to provide a unique inbred line of corn having the designation 78010.

A further object of this invention is to provide an inbred line with the designation 78010 which has appropriate characteristics that when crossed, as a male parent or female parent, with another corn inbred, the first generation ($F_1$) hybrid thereby produced has advantageous and desirable characteristics.

Another object of this invention is to provide pollen of the inbred line 78010 for fertilization of other varieties of corn to produce first generation ($F_1$) corn hybrids with excellent and improved characteristics.

An even further object of this invention is to provide a process for producing corn hybrids from inbred parental lines, one of which is the inbred line 78010, where as a result of heterosis, first generation ($F_1$) hybrid corn with desirable characteristics such as high yield, better stability, improved insect resistance and disease resistance, and the like results.

These and other objects of the invention are achieved with an inbred line of corn having the designation 78010 with superior yield, excellent stalks, and excellent stay-green characteristics.

This invention in another embodiment provides hybrid corn produced by crossing a first corn line with a second corn line, where the first corn line or the second corn line is the corn inbred line 78010 and the other corn line is an inbred line of corn other than 78010 or is a hybrid corn cross.

In a further embodiment of this invention, this invention provides seed of the inbred line 78010.

In an even further embodiment of this invention, this invention provides pollen of the inbred line 78010, useful in fertilization of other lines of corn to produce seed.

Also an embodiment of this invention is a process for producing a hybrid corn variety comprising:

(a) planting in pollinating proximity seeds of the inbred line 78010 and seeds of another corn line;

(b) cultivating the corn plants resulting from the planting before the time of flowering;

(c) emasculating the plants of either corn line;

(d) allowing cross-pollination to occur between the inbred line 78010 and the other corn line; and (e) harvesting seeds produced on the plants of the emasculated line, with embodiments including the other corn line being a hybrid corn cross or an inbred corn line and with a particularly preferred embodiment being the use of another inbred corn line as the other corn line in the above process.

DETAILED DESCRIPTION OF THE INVENTION

As indicated above, this invention provides a novel inbred line 78010 useful as a parental line by crossing with other corn lines, particularly corn inbred lines, to produce first generation ($F_1$) corn hybrids. Although generally the inbred line 78010 is employed as a female parent in the cross-breeding, if desired, the inbred line 78010 can be employed as a male parent.

The inbred corn line 78010 is a yellow dent corn inbred line and was developed as indicated below:

A cross of hybrid lines A634 (as the male) and B73 (as the female), publically available respectively from the University of Minnesota, St. Paul, Minn. and Iowa State University, Ames, Iowa, using conventional cross hybridization techniques was made. More specifically, the cross B73 (Iowa Stiff Stalk Synthetic)×A634 was made at Dayton, Iowa. S0 generation seed from the harvested ears was bulked. Seed of the S0 generation cross was sent to Homestead, Fla., for self pollination. All harvested ears were returned to Dayton, Iowa, shelled and the S1 generation seed bulked. The S1 generation seed was planted at Dayton, Iowa, in a single row and the plants were self pollinated. Three self pollinated ears (S2 generation seed) were harvested, shelled separately, and the S2 seed maintained separately.

S2 generation seed of ear number one (of three harvested) was planted at Homestead Fla., in a five row block and the plants self pollinated. Five self pollinated ears were harvested and returned to Dayton, Iowa. Seed of each ear was shelled separately and the S3 generation seed maintained separately. S3 generation seed of ear number three (of the five harvested) was planted at Dayton, Iowa, in a two row block and the plants self pollinated. Four self pollinated ears were harvested, shelled separately, and the S4 generation seed maintained separately.

S4 generation seed of ear number four (of the four harvested) was planted at Homestead, Fla., in a single row and the plants self pollinated. One self pollinated ear was harvested and returned to Dayton, Iowa, and the S5 generation seed shelled and maintained. S5 generation seed from the single ear was planted at Dayton, Iowa, in a single row and the plants self pollinated. No ears were harvested. S5 generation seed was planted in Hawaii in a single row and the plants self pollinated. Nine ears were harvested, returned to Dayton, Iowa, shelled and the seed bulked. The seed was coded 78010. A pure source of 78010 has been maintained by self pollinating and bulking seed from selected ears from each generation.

Seeds of this inbred line developed as a result of the above inbreeding have been deposited in the American Type Culture Collection, 12301 Parklawn Drive, Rockville, Md. 20852, and have received accession No. 40182.

The cells of plants of inbred line 78010 which can be grown in culture and differentiated or regenerated to form plants of the inbred line also constitute a part of this invention. For details of generation procedures see C. E. Green and C. A. Rhodes, "Plant Regeneration In Tissue Culture of Maize", 1982, *Maize for Biological Research*, ed. W. F. Sheridan, Plant Molecular Biology Association, Charlottesville, Va. pp. 367-372.

As indicated above, inbred line 78010 is a yellow dent corn appropriately adapted for growth in the Northern Corn Belt of the United States, particularly in Iowa. This inbred line has the following characteristics:

Maturity

Days from emergence to 50% of plants in silk: 81 days/1382 heat units.

74 Days from 50% silk to harvest at 25% by weight kernel moisture:
81 days/1339 heat units.

Plant

Height (to flag leaf): 140 cm
Ear Height (to base of top ear): 80 cm
Number of Tillers: None
Number of Ears Per Stalk: two-ear tendency
Cytoplasm Type: Normal

Leaf

Color: Medium green (WF9)
Angle From Stalk: <30°
Sheath Pubscence: Medium (WF9)
Width: Widest point of ear node leaf: 9 cm
Number of leaves per mature plant: 20

Tassel

Number of Lateral Branches: 6
Branch Angle from Central Spike: <30°
Pollen Shed: Light (WF9)
Anther Color: Purple
Glume Color: Green

Ear (Husked Ear Data Unless Otherwise Stated)

Length 16 cm
Mid-point Diameter: 42 mm
Weight: 119 gm
Kernel Rows: 16; distinct; slightly curved
Silk Color (exposed at Silking Stage): green-yellow
Husk Extension (Harvest Stage): Medium (Barely covering Ear)
Husk Leaf: Short (<8 cm)
Shank: 9 cm long; Internodes: 5
Taper: Average

Kernel (Dried)

Size (from Ear Mid-Point): 10 mm long; 8 mm, wide; 5 mm, thick
Shape Grade (% rounds): 60-80
Pericarp Color: Colorless
Aleurone Color: Homozygous; White
Endosperm Color: Yellow, While cap.
Endosperm Type: Normal Starch
Weight/100 Seeds (Unsized Sample): 34 gm

Cob

Diameter at Mid-point: 26 mm
Strength: Strong
Color: Red

Disease Resistance

Anthracnose (foliar phase): Resistant
Southern Leaf Blight (Race 0): Resistant
Eyespot: Resistant

Varieties Most Closely Resembling Corn Inbred Line 78010 for the Characteristics Given:

| Character | Variety |
| --- | --- |
| Maturity | A634Ht |
| Plant Type | A634Ht |
| Ear Type | B73 |

Heat units calculations are derived by using the following formula: GDD equals [Daily Maximum Temperature (86° F.) plus Daily Minimum Temperature (50° F.)] divided by 2 minus 50° F.

Inbred corn line 78010 is a yellow dent corn inbred line. The closest known inbred line is A634Ht. Inbred line 78010 is statistically significantly different from known inbred line A634Ht in terms of plant height (140 cm versus 159 cm); leaf angle from stalk (23.7° versus 44.3°); anther color (purple versus green-yellow) and silk color (green-yellow versus purple). Further, this inbred line has distinct characteristics in the ear diameter (42 versus 38 mm) and the weight per 100 seeds (34.1 versus 29.3 gm).

These characteristics of inbred line 78010 versus publicly known inbred line A634Ht are summarized in Table 1 below:

TABLE 1

| | 78010 vs. A634Ht | | |
|---|---|---|---|
| Plant and Ear Characteristics | 78010 | A634Ht | Testing Hypothesis $H_0: \mu_1 = \mu_2$ $H_A: \mu_1 \neq \mu_2$ |
| 1. Plant height (cm) | 140 | 159 | Sig. ($\alpha = 0.1$) |
| 2. Leaf angle from stalk (°) | 23.7° | 44.3° | Sig. ($\alpha = 0.1$) |
| 3. Anther color | purple | green-yellow | |
| 4. Ear diameter (mm) | 42 | 38 | Sig. ($\alpha = 0.1$) |
| 5. Silk color. | green-yellow | purple | |
| 6. Kernel weight per 100 Seeds (gm) | 34.1 | 29.3 | Sig. ($\alpha = 0.1$) |

(1) $N_1 \neq N_2$

Isozyme analysis of inbred lines 78010 and A634Ht shows that genetic differences exist in at least four different loci, AcPH—2 versus 4; Idh B—6 versus 4 MDHB—3.5 versus 6 and PHI—5 versus 4.

Isozyme genotypes of inbred line 78010 in comparison with known inbred lines B73Ht and A634Ht are shown in Table 2 below:

TABLE 2

| Isozyme Genotypes of Selected DEKALB Parents | | | |
|---|---|---|---|
| | Alleles Present | | |
| LOCUS | 78010 | B73Ht | A634Ht |
| # of plants assayed | 6 | 6 | 6 |
| ACPH | 2 | 2 | 4 |
| ADH | 4 | 4 | 4 |
| Cat | 9 | 9 | 9 |
| EP | 6 | 6 | 6 |
| GOT U | 4 | 4 | 4 |
| GOT M | 4 | 4 | 4 |
| GOT L | 4 | 4 | 4 |
| B-Glu | 7 | 7 | 7 |
| IDH A | 4 | 4 | 4 |
| IDH B | 4 | 4 | 6 |
| MDH A | 6* | 6* | 6* |
| MDH B | 3.5 | 3.5 | 6 |
| MDH C | 16 | 16 | 16 |
| MDH D | 12 | 12 | 12 |
| MDH E | 12 | 12 | 12 |
| PGM A | 9 | 9 | 9 |
| PGM B | 4 | 4 | 4 |
| PHI | 4 | 4 | 5 |

*Allele is probably 6 but null cannot be ruled out.
The technique of using isozymes for genotyping or "fingerprinting" is described by the following reference:
Goodman, M. M. and C. W. Stuber. 1980 Genetic identification of lines and crosses using isoenzyme electrophoresis. Proceedings of the Thirty-fifth Annual Corn and Sorghum Industry Research Conference.

Inbred line 78010 is an advantageous parental line for use in production of hybrid corn, particularly first generation (F₁) hybrid corn. Where this inbred line is employed, it is employed with another inbred line, for example, and the two inbred lines are cross-hybridized using conventional techniques. More specifically, two inbred lines as parents, one of which is the inbred line 78010, are planted in pollinating proximity to each other. This can be achieved by planting the parental lines in alternating rows, in blocks or in any other convenient planting pattern. The plants of both lines are both allowed to grow until the time of flowering. Advantageously, during this growth stage, the plants are generally thinned at about the 3-leaf stage and are also in general treated with fertilizer and/or other agricultural chemicals as considered appropriate by the grower.

At the time of flowering, in the event that inbred line 78010 is employed as the male parent, the tassels of the other parental line are removed from all plants of the other parental line employed as the female parent line. The detasseling can be achieved manually but also can be done by machine if desired. Alternatively, chemical sterilization or conversion of the female parent by addition of a cytoplasmic male sterile trait can be used. When inbred line 78010 is employed as the female parent, its tassels will be removed and the other parental line will be allowed to produce pollen normally.

In either case, the lines are then allowed to continue to grow and natural cross-pollination occurs as a result of the action of wind which is normal in the pollination of grasses, including corn. As a result of the emasculation of the female parent line, all the pollen from the male parent line is available for pollination since tassels and thereby pollen bearing flowering parts have been previously removed from all plants of the inbred line being used as the female in the hybridization. Of course, it would be obvious during this hybridization procedure, the parental varieties are grown such that they are isolated from other corn fields to prevent any accidental contamination of pollen from foreign sources. Isolation techniques are well within the skill of those skilled in this art.

Both of the parent inbred lines of corn are allowed to continue to grow until maturity but only the ears from the female inbred line as a parent are harvested to obtain seeds of a novel F₁ hybrid corn. If desired, corn produced in the male parent variety can be harvested, e.g., for grain use, but these seeds are not useful as hybrid seeds.

The novel F₁ hybrid seed produced can then be planted in a subsequent growing season with the desirable characteristics in terms of F₁ hybrid corn plants providing improved grain yields being achieved.

The inbred line 78010 has been employed to produce novel F₁ corn plants with markedly advantageous characteristics, i.e., by utilizing inbred line 78010 as the female parent inbred line with proprietary inbred line 78060A as the male parent. This first generation (F₁) corn hybrid designated DK524 is the subject of a co-pending patent application Ser. No. 727,632, filed Apr. 26, 1985, the disclosure of which is herein incorporated by reference.

The characteristics of first generation (F₁) hybrid DK524 in comparison with identically obtained results on a DeKalb-Pfizer Genetics commercial variety T1000 both of which mature at a similar rate and thus are appropriate for comparison, are shown in Table 3 below.

TABLE 3

| Hybrid | Yield in Bushels | Kernel Moisture Percent | Plant Height Inches | Ear Height Inches | Stay Green | Not Stalk Lodged | Yield Moisture |
|---|---|---|---|---|---|---|---|
| DK524 | 137.4 | 23.0 | 91.2 | 44.5 | 96.3 | 99.5 | 114.0 |
| T1000 | 121.2* | 23.3* | 78.9* | 34.6* | 85.9* | 100.1* | 98.9* |

\* = Statistically significant at the 1% level.

From the above, it can be seen that the inbred line 78010 provides advantageous breeding stock for use as a parental line as a female parent, to provide first generation hybrids with unique and desirable characteristics. It will be equally advantageous to use the line as a male parent.

While the invention has been described in detail and with respect to specific embodiments thereof, it would be apparent to one skilled in the art that various changes and modifications can be made therein without the departing from the spirit and scope thereof.

I claim:

1. An inbred corn line having the designation 78010.
2. A plant of the inbred corn line having the designation 78010 of claim 1.
3. Seeds of the inbred corn line having the designation 78010 of claim 1.
4. Pollen of the inbred corn line having the designation 78010 of claim 1.
5. A plant cell which, upon growth and differentiation, produces the plant of claim 2.
6. First generation (F$_1$) hybrid corn seed produced by crossing a first inbred corn line as a male parent with a second inbred corn line as a female parent, one of said inbred corn lines being said inbred line 78010.
7. The seed of claim 6, wherein said inbred line 78010 is the female parent.
8. A process for producing hybrid corn comprising:
   (a) planting in pollinating proximity seeds of inbred corn line having the designation 78010 of claim 1 and another line of corn;
   (b) cultivating corn plants resulting from the planting before the time of flowering;
   (c) emasculating the plants of either the inbred corn line 78010 or of said other corn line;
   (d) allowing cross-pollination to occur between said corn lines and
   (e) harvesting seeds produced by said plants of the corn line which was emasculated in step (c).
9. The process of claim 8, wherein said other line of corn is an inbred line of corn other than said inbred corn line 78010.
10. The process of claim 9, wherein said process comprises in step (c) emasculating the plants of said other line of corn.

* * * * *